(12) United States Patent
Gunatillake et al.

(10) Patent No.: US 6,437,073 B1
(45) Date of Patent: Aug. 20, 2002

(54) NON-ELASTOMERIC POLYURETHANE COMPOSITIONS

(75) Inventors: Pathiraja A. Gunatillake, Mulgrave (AU); Simon John McCarthy, Portland, OR (US); Raju Adhikari, Wheelers Hill; Gordon Francis Mejis, Murrumbeena, both of (AU)

(73) Assignee: Aortech Biomaterials PTY Ltd. (AU)

( * ) Notice: Subject to any disclaimer, the term of this patent is extended or adjusted under 35 U.S.C. 154(b) by 0 days.

(21) Appl. No.: 09/677,394

(22) Filed: Sep. 29, 2000

Related U.S. Application Data

(63) Continuation of application No. PCT/AU99/00236, filed on Mar. 30, 1999.

(30) Foreign Application Priority Data

Mar. 31, 1998 (AU) .............................................. PP2688

(51) Int. Cl.$^7$ .............................................. C08G 18/61
(52) U.S. Cl. ........................... 528/28; 607/9; 623/2.42; 623/3.29; 623/18.11; 623/926
(58) Field of Search ............................. 528/28; 607/9; 623/242, 3.29, 18.11, 926

(56) References Cited

U.S. PATENT DOCUMENTS

| | | | |
|---|---|---|---|
| 4,647,643 A | 3/1987 | Zdrahala et al. | 528/28 |
| 4,758,601 A | 7/1988 | Haas et al. | 521/108 |
| 5,128,408 A | 7/1992 | Tanaka et al. | 525/54.2 |
| 5,252,683 A | 10/1993 | Murata et al. | 525/458 |

FOREIGN PATENT DOCUMENTS

| | | | |
|---|---|---|---|
| AU | 199741924 | 4/1998 | C08G/18/44 |
| EP | 0230666 A2 | 8/1987 | C08G/18/10 |
| EP | 0773246 A1 | 5/1997 | C08G/18/12 |

OTHER PUBLICATIONS

Yilgor, Wilkes, McGrath; Polymer Preprints; 23(1); 1982; pp. 286–288.*
"Derwent abstract for Japanese Patent No. JP 4180914 A", 1 Page, (Jun. 29, 1992).
"Derwent abstract for Japanese Patent No. JP 4292676", 1 Page, (Oct. 16, 1992).
"Derwent abstract for Japanese Patent No. JP 63179916", 1 pg, (Jul. 23, 1998).

* cited by examiner

Primary Examiner—Rachel Gorr
(74) Attorney, Agent, or Firm—Schwegman, Lundberg, Woessner & Kluth, P.A.

(57) ABSTRACT

A non-elastomeric polyurethane composition which includes a first chain extender of the general formula (I)

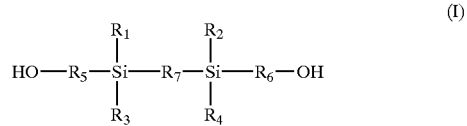

Figure 1:
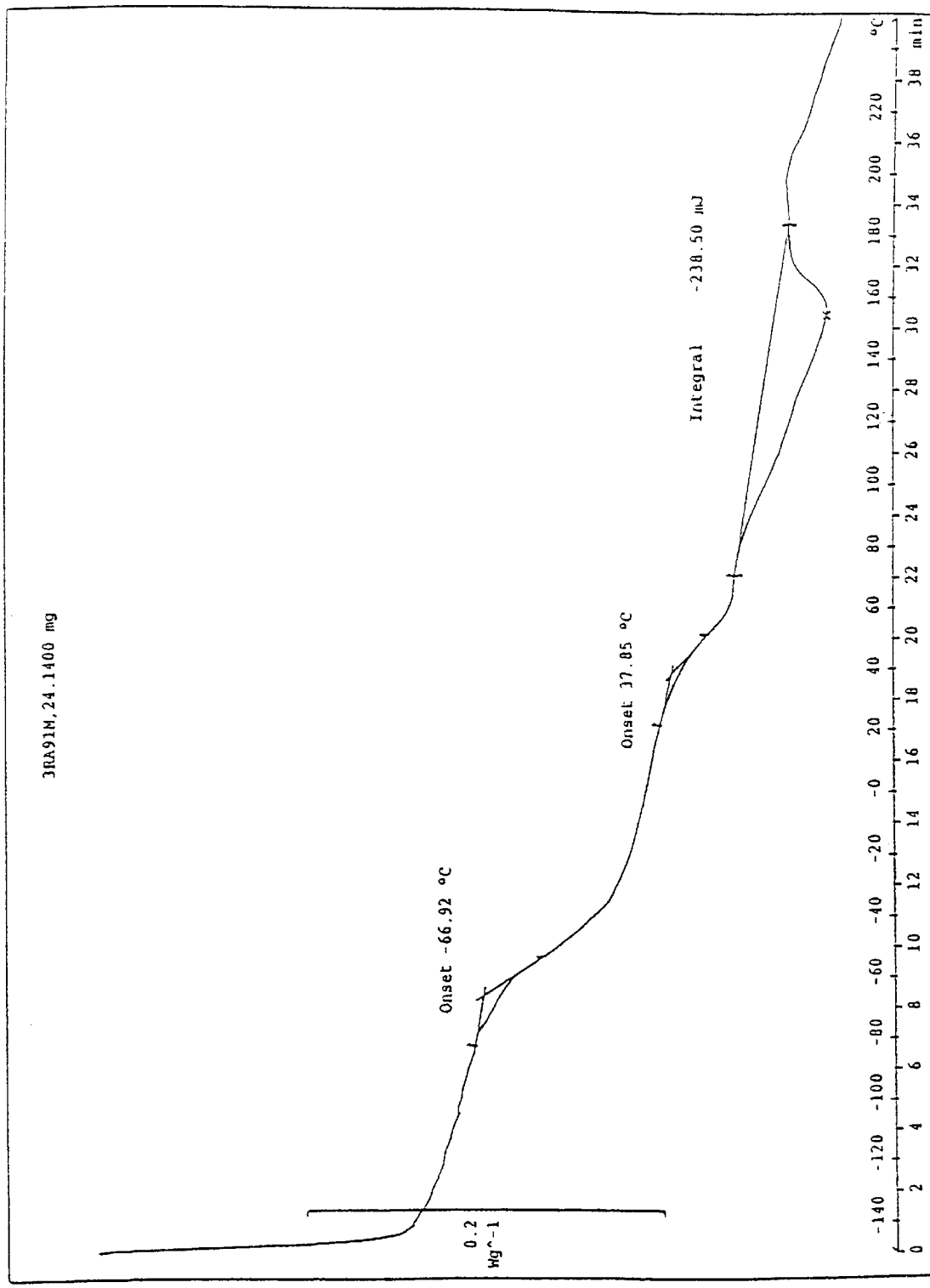

wherein
$R_1$, $R_2$, $R_3$, $R_4$, $R_5$, and $R_6$ are the same or different and selected from an optionally substituted straight chain, branched or cyclic, saturated or unsaturated hydrocarbon radical;
$R_7$ is a divalent linking group or an optionally substituted straight chain, branched or cyclic, saturated or unsaturated hydrocarbon radical; and
n is 0 or greater, and a second chain extender.

18 Claims, 1 Drawing Sheet

NON-ELASTOMERIC POLYURETHANE COMPOSITIONS

This application is a continuation of International Patent Application No. PCT/AU99/00236, filed on Mar. 30, 1999, which in turn is an international filing of Australian Application No. PP2688, filed on Mar. 31, 1998, all of which are incorporated herein by reference.

CROSS-REFERENCE TO RELATED APPLICATIONS

The present invention relates to non-elastomeric polyurethane compositions based on silicon-containing chain extenders characterised by high flexural modulus, high glass transition and heat distortion temperatures. These polyurethane compositions are useful for applications requiring high impact resistance, flexural strength, and other structural properties similar to engineering thermoplastics, and in particular for use in above ambient temperature end-use environments.

Polyurethanes represents a broad class of materials formed by reacting chemical compounds bearing functional groups such as isocyanate and hydroxyl. A wide range of polymers with a variety of properties ranging from elastomers to rigid materials can be prepared by selecting a suitable combination of reagents in various proportions. Of these materials, polyurethane elastomers formed by reacting a polyol (typical molecular weight 500 to 4000) with a diisocyanate and a chain extender (low molecular weight diol of molecular weight less than 500), form an important class of commercially useful materials. The methods of synthesis and studies on structure property relationships of these materials are abundant in the polyurethane literate[1].

The polyurethanes formed by reacting only the chain extender and the diisocyanate are generally very rigid with high flexural modulus, and are often difficult to process due to high melting temperatures. For example, a polyurethane prepared from a common diisocyanate 4,4'-methylenediphenyldiisocyanate (MDI) and 1,4-butanediol (BDO) generally melts at temperatures above 210° C. which is well above the thermal decomposition temperature of the urethane linkage[2]. Further, such materials are generally very brittle and have poor mechanical properties. Alternatively, harder grades of polyurethane elastomers prepared using a relatively lower proportion of the polyol component usually have a low heat distortion temperatures, primarily due to the presence of the polyol component, usually with a glass transition below ambient temperature.

Development of polyurethane compositions with high flexural modulus combined with high heat distortion temperatures and thermal processability would provide a new range of rigid materials with strength required for applications in high temperature end-use environments.

The hard polyurethane compositions disclosed in U.S. Pat. No. 4,101,529 are made by reacting polyisocyanates with mixtures of cycloaliphatic diols and low molecular weight diol chain extenders such as ethylene glycol and low molecular weight active hydrogen containing materials such as trimethylolpropane, and optionally a polymeric polycaribonate diol. These compositions are characterised by heat distortion temperature of at least 88° C. (measured by ASTM D-648 at 264 psi) and hardness of at least 75 Shore D. Similarly, U.S. Pat. No. 4,808,690 discloses polyurethane compositions with high heat distortion temperatures that are highly cross-linked, and are made by reacting a polyisocyanate prepolymer and a polyhydric alcohol having from 2 to 8 hydroxyl groups in combination with a polyester polyol. Such polyurethanes are expected to be difficult to thermally process due to their highly cross-linked nature.

U.S. Pat. No. 4,822,827 describes thermoplastic polyurethane compositions with high glass transition temperatures based on reacting a polyisocyanate and a particular combination of chain extenders including cycloalkane diol, optionally in the presence of a minor amount of high molecular weight polyol. It is also disclosed that only certain members of the new polymers are optically clear.

The compositions disclosed in U.S. Pat. No. 4,101,529, U.S. Pat. No. 4,393,186, U.S. Pat. No. 4,808,690 and U.S. Pat. No. 4,822,827 all contain a polyol for example polyester, polycarbonate or polyether as part of the polyurethane structure. This would make the prior art compositions susceptible to possible degradation under oxidative and hydrolytic environments, particularly high temperature environments which may limit their applications. Development of new polyurethane compositions which are free of segments derived from polyols while overcoming most of the disadvantages of the prior art compositions, would broaden the applications of these materials to areas such as medical devices and implants.

Accordingly, a requirement exists to develop polyurethanes which are easily processable and have a high flexural modulus, high heat distortion temperature, optical clarity, and resistance to degradation.

According to one aspect, the present invention provides a non-elastomeric polyurethane composition which includes a chain extender of the general formula (1)

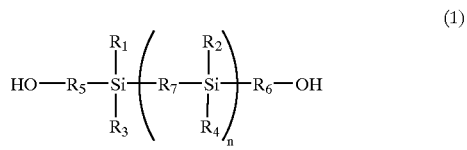

(1)

wherein

R$_1$, R$_2$, R$_3$, R$_4$, R$_5$ and R$_6$ are the same or different and selected from an optionally substituted straight chain, branched or cyclic, saturated or unsaturated hydrocarbon radical;

R$_7$ is a divalent linking group or an optionally substituted straight chain, branched or cyclic, saturated or unsaturated hydrocarbon radical; and n is 0 or greater, preferably 2 or less.

The term "non-elastomeric" in the present context refers to polyurethanes having a % elongation of up to about 200%, generally up to about 100%.

The term "chain extender" in the present context means any compound having at least two functional groups per molecule capable of reacting with the isocyanate group and generally in the molecular weight range 60 to about 500, more preferably 60 to about 450.

Preferably, the chain extender of formula (1) has a molecular weight of about 500 or less.

The hydrocarbon radical for substituents $R_1$, $R_2$, $R_3$ and $R_4$ may include alkyl, alkenyl, alkynyl, aryl and heterocyclyl radicals. It will be appreciated that the equivalent radicals may be used for substituents $R_5$, $R_6$ and $R_7$ except that the reference to alkyl, alkenyl and alkynyl should be to alkylene, alkenylene and alkynylene, respectively. In order to avoid repetition, only detailed definitions of alkyl, alkenyl and alkynyl are provided hereinafter.

The term "alkyl" denotes straight chain, branched or mono- or poly-cyclic alkyl, preferably $C_{1-12}$ alkyl or cycloalkyl. Examples of straight chain and branched alkyl include methyl, ethyl, propyl, isopropyl, butyl, isobutyl, sec-butyl, amyl, isoamyl, sec-amyl, 1,2-dimethylpropyl, 1,1-dimethylpropyl, pentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-methylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- 3- or 4-propylheptyl, undecyl 1-, 2-, 3-, 4-, 5-, 6-, 7-, 8- or 9-methyldecyl 3-, 4-, 5-, 6- or 7-ethylnonyl, 1-, 2-, 3-, 4- or 5-propyloctyl, 1-, 2-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6, 7- or 8-ethyldecyl, 1-, 2-, 3-, 4-, 6-propylnonyl, 1-, 2-, 3- or 4-butyloctyl, 1,2-pentylheptyl and the like. Examples of cyclic alkyl include cyclopropyl, cyclobutyl, cyclopentyl, cyclohexyl, cycloheptyl, cyclooctyl, cyclononyl, cyclodecyl and the like.

The term "alkenyl" denotes groups formed from straight chain, branched or mono- or poly-cyclic alkenes including ethylenically mono- or poly-unsaturated alkyl or cycloalkyl groups as defined above, preferably $C_{2-12}$ alkenyl. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cycloocta-tetraenyl and the like.

The term "alkynyl" denotes groups formed from straight chain, branched, or mono or poly-cyclic alkynes. Examples of alkynyl include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecynl-3-methyl-1-dodecyn-3-yl-, 2-tridecynyl, 11-tridecynyl, 3-tetradecynyl, 7-hexadecynyl, 3-octadecynyl and the like.

The term "aryl" denotes single, polynuclear, conjugated and fused residues of aromatic hydrocarbons. Examples of aryl include phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl and the like.

The term "heterocyclyl" denotes mono- or poly-cyclic heterocyclyl groups containing at least one heteroatom selected from nitrogen, sulphur and oxygen Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated 3 to 6-membered heteromonocyclic groups containing 1 to 4 nitrogen atoms, such as pyrrolidinyl, imidazolidinyl, piperidino or piperazinyl; unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl; unsaturated 3 to 6-membered heteromonocyclic group containing an oxygen atom, such as, pyranyl or furyl; unsaturated 3 to 6-membered hetermonocyclic group containing 1 to 2 sulphur atoms, such as, thienyl; unsaturated 3 to 6-membered heteromonocyclic group containing 1 to 2 oxygen atoms and 1 to 3 nitrogen atoms, such as, oxazolyl, isoazolyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heteromonocyclic group containing 1 to 2 sulphur atoms and 1 to 3 nitrogen atoms, such as thiazolyl or thiadiazolyl; saturated 3 to 6-membered heteromonocyclic group containing 1 to 2 sulphur atoms and 1 to 3 nitroaen atoms, such as, thiadiazolyl; and unsaturated condensed heterocyclic group containing 1 to 2 sulphur atoms and 1 to 3 nitrogen atoms, such as benzothiazolyl or benzothiadiazolyl.

In this specification, "optionally substituted" means that a group may or may not be further substituted with one or more groups selected from oxygen, nitrogen, sulphur, alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy, haloalkoxy, haloalkenyloxy, haloalkynyloxy, haloaryloxy, nitro, nitroalkyl, nitroalkenyl, nitroalkynyl, nitroaryl, nitroheterocyclyl, azido, amino, aylanino, alkenylamino, alkylamtio, arylamino, benzylamino, acyl, alkenylacyl, alkynylacyl, arylacyl, acylamnino, acyloxy, aldehydo, alkylsuiphonyl, arylsulphonyl, alkyLsophonylamino, arylsulphonylamino, alkylsuiphonyloxy, arylsulphonyloxy, heterocyclyl, heterocycloxy, heterocyclylamino, haloheterocyclyl, alkylsulphenyl, arylsuiphenyl, carboalkoxy, carboaryloxy, mercapto, alkylthio, arylthio, acylthio and the like.

Suitable divalent linking groups for $R_7$ include O, S and NR wherein R is hydrogen or an optionally substituted straight chain, branched or cyclic, saturated or unsaturated hydrocarbon radical.

Preferred chain extenders of formula (1) are 1,3-bis(4-hydroxybutyl)-tetarethyl disiloxane (compound of formula (1) wherein $R_1$, $R_2$, $R_3$ and R are methyl, $R_5$ and $R_6$ are butyl and $R_7$ is O), 1,4-bis(3-hydroxypropyl)tetramethyl disilylethylene (compound of formula (1) wherein $R_1$, $R_2$, $R_3$ and $R_4$ are methyl, $R_5$ and $R_6$ are propyl and $R_7$ is ethylene) and 1,4-bis(3-hydroxypropyl)tetramethyl disiloxane.

In a preferred embodiment, the chain extender of formula (1) defined above is combined with a chain extender known in the art of polyurethane manufacture.

According to another aspect the present invention provides a non-elastomeric polyurethane composition which includes a chain extender of general formula (1) defined above and a chain extender known in the art of polyurethane manufacture.

The chain extender known in the art of polyurethane manufacture is preferably selected from the group comprising 1,4-butanediol, 1,6-hexanediol, 1,8-octanediol, 1,9-nonanediol, 1,10-decanediol, 1,12-dodecanediol, 1,4-cyclohexanedimethanol, 1,4-cyclohexanediols and isomers thereof, hydroxyquinone bix(2-hydroxyethyl)ether, 2-ethyl-1,3-hexanediol, 2-butyl-2-ethyl-1,3-propanediol, 2,2,4-trimethyl-1,3-pentanediol and mixtures thereof 1,4-cyclohexanedimethanol and 1,4 butanediol are especially preferred.

The silicon chain extender can be used alone or in a range of combinations with known chain extenders. Higher molar percentages of the conventional chain extenders, particularly cycloalkane diols, lead to polyurethane compositions with improved mechanical properties and heat distortion temperatures. Accordingly, a preferred chain extender combination includes a silicon chain extender of formula (1) and a cycloalkane diol chain extender.

Although the preferred chain extender mixture contains one silicon chain extender of formula (1) conventional chain extender, it is understood that mixtures containing more than two diols may be used in formulations.

The silicon chain extender can be conveniently prepared by methods reported in the literature[3]. Further, the compounds such as 1,3-bis(3-hydroxypropyl)tetramethyl disiloxane (BPTD) and 1,3-bis(4-hydroxybutyl)tetramethyldisiloxane (BHTD) are available commercially. A range of such silicon-based chain extenders can also be prepared by using hydrosilylation reaction of the appropriate hydroxy alkene and 1,1,3,3-tetramethyldisiloxane using catalyst such as the Wilkinson's catalyst.

The polyurethane composition of the present invention generally also includes a polyisocyanate.

Thus, the present invention also provides a non-elastomeric polyurethane composition which includes a chain extender of formula (1) defined above and a polyisocyanate.

The polyisocanates that can be used in the present invention are preferably diisocyanates. The diisocyanates useful in the present invention include aliphatic or aromatic diisocyanates such as:

4,4'-diphenylnethane diisocyanate (MDI);
methylene bis(cyclohexyl)diisocyanate ($H_{12}MDI$) including the 4,4' isomer, the 2,4'-siomer and mixtures thereof, the geometrical isomers, trans/trans, cis/trans, cis/cis and mixtures thereof,
p-phenylene diidocyanate (pPDI);
trans-cyclohexane-1,4-diisocyanate (CHDI);
1,6-diisocyanatohexane (DICH);
1,6-toluene diisocyanate (2,4-TDI);
para-tetramethylxylene diisocyanate p-TMXDI) and meta-tetramethylxylene diisocyanate (m-TMXDI);
2,4- and 2,6-toluene diisocyanate and their isomer mixtures;
isophorone diisocyanate; and
1,5-napthalene diisocyanate.

It will be appreciated that this list is not exhaustive and that the invention encompasses any polyisocyanates known to be suitable in the manufacture of polyurethanes.

The polyurethanes of the present invention may be prepared by any suitable known technique familiar to those skilled in the manufacture of polyurethanes. These methods include manual or mechanical mixing with or without any solvents present, casting, reaction extrusion and reaction injection moulding. A preferred method involves mixing the chain extender/or mixture with a polyisocyanate, preferably a diisocyanate, directly. The silicon chain extender is preferably degassed under vacuum at ambient temperature prior to the polymerisation If desired, a catalyst such as dibutyltin dilaurate at a level of 0.001 to about 0.5 wt % based on the total ingredients and any other desirable additives (eg: antioxidants) may be added to the initial mixture. The appropriate amount of diisocyanate is then added to the silicon chain extender and stirred rapidly to form a clear solution, usually about 30 to 90 seconds, and the polymer cured in an oven at temperatures between 40 and 120° C.

When mixtures of chain extenders are used the polymerisation may be carried out, first by preparing the chain extender mixture with the desired proportions and then vacuum degassing, followed by adding to the diisocyanate. Alternatively, the preferred method is to add the silicon chain extender first to the diisocyanate and sting the mixture until the solution becomes clear, and the second chain extender is added quickly afterwards with stirring.

Thus, the polyurethane composition of the present invention may be further defined as comprising a reaction product of:

(i) a diisocyanate or a polyisocyanate; and
(ii) a silicon chain extender or a chain extender mixture defined above.

In another aspect, the present invention provides a method of producing a polyurethane including reacting a polyisocyanate with a silicon chain extender or a mixture of chain extenders including a silicon chain extender.

The amounts of the chain extender or mixture of chain extenders and diisocyanate or polyisocyanate are chosen, so that the number of moles of the chain extender functional groups (for example hydroxyl groups) are equal to the number of moles of the isocyanate functional groups. It is understood in the art of making polyurethanes that a small excess of about 5 mol % of either the chain extender or the diisocyanate may be used. When mixtures of two or more chain extenders are used, any combination of chain extender molar ratios could be used provided the total mixture is equimolar with the diisocyanate.

The polyurethanes may be processed by conventional methods such as extrusion, injection and compression moulding without the need of processing waxes. If desired, however, conventional polyurethane additives such as catalysts, antioxidants, stabilisers, lubricants, dyes, pigments, inorganic and/or organic fillers, and reinforcing materials such as impact modifiers can be incorporated into the polyurethane during preparation.

Polyurethanes of the present invention are easily adaptable to a variety of fabrication techniques including solvent casting, blow moulding, machining to various shapes and other conventional processing techniques such as injection moulding and extrusion.

The polyurethane compositions of the present invention are particularly useful in preparing materials having good mechanical properties and clarity, in particular for applications requiring high impact resistance, stiffness, high heat distortion temperature and other structural strength properties similar to polycarbonate, nylon and other engineering thermoplastics. A particularly useful application is in biomaterials, especially for devices and implants requiring one or more of the aforementioned properties.

According to another aspect of this invention there is provided a material having improved mechanical properties, clarity and/or degradation resistance comprising a polyurethane composition which includes a silicon chain extender or a mixture of chain extenders as defined above.

The present invention provides a series of compositions having good mechanical properties, high heat distortion temperature, high flexural modulus, and preferably free of functional groups such as ester, carbonate, and ether making the materials resistant to degradation under oxidative and hydrolytic environments. Further, the polyurethane composition should also show excellent compatibility and stability in biological environments, particularly when implanted in vivo for extended periods of time. Most preferably, the compositions of the present invention are substantially free of segments derived from polyols having a molecular weight in excess of 500.

Accordingly, the compositions may be used as a biomaterial and the term "biomaterial" is used herein in its broadest sense referring to a material which is used in situations where it comes into contact with the cells and/or bodily fluids of living animals or humans. Thus, the polyurethane compositions in this invention are useful in manufacturing medical devices and implants.

In a further aspect, the present invention provides a medical device, article or implant composed wholly or partly of the polyurethane composition described herein.

The medical devices, articles or implants may include components of cardiac pace makers, cardiac assist devices, heart valves, extra-corporeal devices, blood pumps, balloon pumps, A–V shunts, biosensors, artificial joints, and orthopaedic implants. Because of the inherent high heat distortion temperatures of these materials it is expected that the polyurethanes are particularly useful for devices requiring dimensional stability at temperatures such as the human body temperature.

It is understood that the materials in the present invention will also have applications in the non-medical areas particularly requiring high strength, high flexural modulus, and high heat distortion temperature. Such applications may include their use in the manufacture of structural components for pumps, vehicles, mining screens, laminating compounds, for example in glazing, and etc.

According to yet a further aspect, the present invention provides an article composed wholly or partly of the polyurethane composition described herein.

The following examples will illustrate the scope of the present invention. These examples are not to be considered as limiting the invention in any way.

In the examples, reference will be made to the accompanying drawing in which:

FIG. 1 is a DSC thermogram of the polyurethane formed according to U.S. Pat. No. 4,647,643.

EXAMPLE 1

Three polyurethanes compositions were prepared using 4,4'-methylenediphenyl diisocyanate (MDI) and three different chain extender combinations. The three combinations were 1,3-bis(4-hydroxybutyl)tetramethyidisiloxane (BHTD) and 1,4-cyclohexanedimethanol (CHDM as a mixture of cis and trans isomers) in BHTD:CHDM molar ratios of 1:0, 1:1 and 1:3.

BHTD (Silar Laboratories) was degassed at ambient temperature under vacuum (0.1 torr) for 1 h prior to polymerisation. CHDM (Aldrich) was melted at 60° C. and degassed under vacuum (0.1 torr) for 1 h.

All three compositions were prepared by a one-step bulk polymerisation procedure without the use of any catalysts. For the first composition, degassed BHTD (55.68 g) was added to molten (50° C.) MDI (50.00 g) in a polypropylene beaker and stirred rapidly until the solution turns clear. After about 3 min of mixing the viscous polymer was poured onto a teflon-coated tray and curd at 100° C. for 6 hours under nitrogen. The cured polymer was a clear and transparent solid. The second composition (BHTD:CHDM=1:1) was prepared first by adding BHTD (27.821 g) into molten MDI (50.00 g) and string until the solution cleared (about 60 sec stirring) followed by adding CHDM (14.406 g). After stirring the mixture for a further 60 sec, the viscous polymer was poured onto a teflon-coated pan and cured under similar conditions.

The third composition was prepared by reacting BHTD (13.91 g), MDI (50.00 g) and CHDM (21.61 g) using a procedure similar to that used to prepare the second composition.

All three materials were compression moulded, at 200° C. to form 1 mm thick rectangular plaques which were clear and transparent Dumbbells punched from this sheet were used to test mechanical properties using an Instron Model 4032 Universal Testing Machine. The thermal transitions of the materials were measured on a Mettler DSC 30 calorimeter in the −150 to 250° temperature range.

Table 1 summarises the molecular weight, mechanical properties and the glass transition temperatures. FIG. 1 shows the DSC traces of the three polyurethane compositions. As seen from the results, all three materials exhibited high tensile strength, flexural modulus and Shore hardness. It is noteworthy that the increasing CHDM proportion increases these properties as well as the glass transition temperature.

TABLE 1

Properties of polyurethane compositions prepared in Example 1

| Property | composition-1 (BHTD:CHDM = 1:0) | composition-2 (BHTD:CHDM = 1:1) | composition-3 (BHTD:CHDM = 1:3) |
|---|---|---|---|
| Shore Hardness (D) | 75 | 84 | 85 |
| Ultimate Tensile Strength (MPa) | 60 | 68 | 77 |
| Young's Modulus (MPa) | 562 | 713 | 648 |
| Elongation at Break (%) | 20 | 31 | 23 |
| Flexural Modulus (MPa) | 1795 | 1940 | 2130 |
| Molecular Weight (MW distribution) | 170000 (1.37) | 119600 (1.51) | 122000 (1.56) |
| Glass Transition Temperature- | | | |
| onset | 30 | 77 | 98 |
| mid point, | 40 | 83 | 105 |
| end point (° C.) | 58 | 88 | 112 |

TABLE 2

Properties of polyurethane compositions prepared in Example 2

| Property | compositions-1 BHTD:BDO = 40:60) | composition-2 (BHTD:BDO = 50:50) | composition-3 (BHTD:BDO = 60:40) |
|---|---|---|---|
| Shore Hardness (D) | 80 | 82 | 80 |
| Ultimate Tensile Strength (MPa) | 62 | 59 | 55 |
| Young's Modulus (MPa) | 576 | 629 | 577 |
| Elongation at Break (%) | 10 | 23 | 12 |
| Flexural Modulus (MPa) | 2140 | 1960 | 1675 |
| Molecular Weight (MW distribution) | 86160 (1.47) | 129990 (1.49) | 84700 (1.48) |
| Glass Transition Temperature- | | | |
| onset, | 67 | 53 | 55 |
| mid point, | 74 | 61 | 61 |
| end point (° C.) | 81 | 69 | 67 |

EXAMPLE 2

Example 2 describes the preparation of three polyurethane compositions based on MDI and three different combinations of BHTD and 1,4-Butanediol (BDO). These included BHTD:BDO molar ratios of 40:60, 50:50 and 60:40. The three compositions were prepared by a one-step bulk polymerisation procedure. Both BDO and BHTD were degassed as described in Example 1.

The first composition (BHTD:BDO=40:60) was prepared by weighing degassed BHTD (22.225 g) and BDO (10.803 g) into a 150 mL polypropylene beaker and adding molten (50° C.) MDI (50.00 g) with rapid stirring. The solution cleared after about 1 min, and stirring continued until the mixture starts to increase viscosity. The viscous polymer was then poured onto a teflon-coated pan and cured at 100° C. in an oven for 6 hours under nitrogen. A similar procedure was used to make compositions 2 and 3, except that BHTD (27.821 g), BDO (9.003 g) and MDI (50.00 g) were used for composition 2 while BHTD (33.385 g), BDO (7.702 g) and MDI (50.00 g) were used for composition 3.

All three materials were compression moulded to clear and transparent 1 mm thick sheets, and dumbbells punched from the sheets were used for testing tensile properties.

Table 2 summarises the GPC molecular weights, tensile properties and thermal transitions measured by DSC. These results demonstrate that the chain extender combination BHTD and BDO also produces materials that are clear and transparent with high flexural modulus, tensile strength and high Shore hardness. Results further demonstrate that the high proposition of the conventional chain extender (BDO) yields materials with improved mechanical properties and increased glass transition temperature.

EXAMPLE 3

This example illustrates the preparation of three polyurethane compositions based the aliphatic diisocyanate hydrogenated MDI ($H_{12}$MDI from Aldrich). The first two compositions were based on a mixture of BHTD and CHDM in 1:3 and 1:1 molar ratios, and the third composition was based on BHTD and BDO in 1:1 molar ratio. The diisocyanate was a mixture of three isomers, and was used as received. BHTD and CHDM were degassed according to procedures described in example I and BDO as in example 2.

The first composition (BHTD:CHDM=1:3) was prepared by reacting BHTD (2.654 g), CHDM (4.1226 g), dibutyltin dilaurate catalyst (0.001 g) and $H_{12}$MDI (10.00 g). The degassed chain extenders and the catalyst were weighed in to a 25 mL polypropylene beaker and the diisocyanate heated to 60° was then added quickly in to the beaker and rapidly stirred for 1 min. The polymer was cured in the beaker by placing in an oven at 100° C. for 12 hours under nitrogen.

A similar procedure was used to prepare second and third compositions, except that the second composition (BHTD:CHDM=1:1) was based on;
(I) 5.308 g of BHTD, 2.748 g CHDM, 0.01 g dibutyltin dilaurate, and
10.00 g $H_{12}$MDI, while the third composition (BHTD:BDO=1:1 was based on;
(ii) 5.308 g of BHTD, 1.717 g BDO, 0.001 g dibutyltin dilaurate, and
10.00 g $H_{12}$MDI.

All three polyurethane compositions were clear, colorless, and transparent. The polyurethanes were compression moulded to 1 mm thick plaques at 200° C., and dumbbells punched from the sheets were tested for tensile properties on an Instron tensile testing machine. Tensile properties, DSC results, and molecular weights of the polyurethanes are summarised in Table 3. It is noteworthy that even with the aliphatic diisocyanate materials with glass transition temperature of nearly 100° C. could be produced

TABLE 3

Properties of polyurethane compositions prepared in Example 3.

| Property | composition-1 (BHTD:CHDM = 25:75) | composition-2 (BHTD:CHDM = 50:50) | composition-3 (BHTD:BDO = 50:50) |
|---|---|---|---|
| Shore Hardness (D) | 75 | 72 | 73 |
| Ultimate Tensile Strength (MPa) | 77 | 67 | 60 |
| Young's Modulus (MPa) | 653 | 613 | 522 |
| Elongation at Break (%) | 15 | 28 | 31 |
| Flexural Modulus (MPa) | 1776 | 1590 | 1720 |
| Molecular Weight (MW distribution) | 143600 (1.61) | 154720 (1.66) | 162390 (1.72) |
| Glass transition Temp. | | | |
| on set, | 94 | 65 | 76 |
| mid point, | 101 | 71 | 83 |
| end point (° C.) | 109 | 77 | 89 |

EXAMPLE 4

Example 4 describes the preparation of a polyurethane composition based on MDI and a mixture of BPTD:CHDM in a molar ratio (25:75). BPTD ((1,3-bishydroxypropyl) tetramethyldisiloxane) was a commercial reagent purchased from ShinEtsu Chemical Company Ltd (Japan). The composition was prepared by a one-step bulk polymerisation procedure, and both CHDM and BPTD were degassed as described in Example 1.

In this example the silicon-based chain extender was added to MDI first followed by the conventional chain extender CHDM. Degassed BPTD (5.005 g) was added to molten (50° C.) MDI (20 g) in a polypropylene beaker and stirred rapidly until the solution turns clear followed by adding CHDM (8.643 g). After about 1 min of stirring, the viscous polymer was poured onto a teflon-coated tray and cured at 100° C. for 6 hours under nitrogen. The cured polymer was a clear and transparent solid.

The material was compression moulded at 200° C. to form a 1 mm thick sheet and dumbbells punched from the sheet were used for testing tensile properties. Ultimate tensile strength 68 MPa, Young modulus 419 MPa, elongation at break 23%, 82 Shore D hardness.

EXAMPLE 5

This example describes the preparation of a polyurethane composition based on MDI and a mixture of 1,4 bis (3-hydroxypropyl)tetramethyldisilylethylene (HTDE) and CHDM the mole ratio of HTDE to CHDM was 25:75.

The composition was also prepared by reacting HTDE (5.245 g), MDI (20 g) and CHDM (8.643 g) using a procedure similar to that described in example 4. The cured polyurethane was compression moulded under similar conditions and tested for its tensile properties. The material showed 67 MPa ultimate tensile strength, 464 MPa Young modulus, 22%, elongation at Break, and 78 Shore D hardness.

EXAMPLE 6

This example illustrates the preparation of a polyurethane based on HTDE:CHDM (25:75) and the aliphatic diisocyanate hydrogenated MDI ($H_{12}$MDI, Aldrich). The polyurethane was prepared by reacting HTDE (2.501 g), CHDM (4.122 g), $H_{12}$MDI(10 g) and dibutyltin dilaurate (0.001 g) and $H_{12}$MDI (10 g). A mixture of the degassed chain extenders and the catalyst were weighed in to a 25 mL polypropylene beaker and the diisocyanate heated to 60° C. was then added immediately into the beaker while stirring simultaneously for 1 min. The polymer was cured in the beaker itself at 100° C. for 12 hours under nitrogen.

The polyurethane was compression moulded at 200° C. to a 1 mm thick plaque and dumbbells punched from the sheet were tested for tensile properties. The material exhibited 70 MPa ultimate tensile strength, 478 MPa Young modulus, 20% elongation at Break and 76 Shore D hardness.

COMPARATIVE EXAMPLE 1

This example demonstrates that the compositions disclosed in the prior art (U.S. Pat. No. 4,647,643) do not provide polyurethanes with high modulus, high heat distortion temperatures or the high mechanical strength that is achievable with compositions disclosed in the present invention.

A polyurethane composition was prepared according to Example 11 of U.S. Pat. No. 4,647,643. The silicon diol (Q4-3667 fluid) used in this example was obtained from Dow Corning Corporation.

The diol Q4-3667 Fluid (7.0 g), Terathane T-1000 (53.0 g) and BDO (6.667 g) were mixed and vacuum stripped (2 torr) at 65° C. for a minimum of 30 minutes until the cessation of bubbling was noted Molten MDI (33.430 g) was quickly added to the mixture and stirred rapidly with a stainless spatula. After about 1 minute, the contents were poured into a teflon coated metal tray and heated to 125° C. in a nitrogen circulating oven for 1 hour to complete the polymerisation. After cooling to room temperature, the material was granulated and dried at 65° C. for 12 hours under vacuum (0.1 torr) before being compression moulded into a flat sheet at temperatures between 190–200° C. under a nominal load of 8 tons.

The polyurethane exhibited 11 MPa ultimate tensile strength, 19 MPa Young's modulus, 520% elongation at break and 35D Shore hardness. The heat distortion temperature of the material was 67° C. as illustrated in FIG. 1. Accordingly, these results clearly demonstrate that U.S. Pat. No. 4,647,643 does not enable the preparation of polyurethane compositions with properties such as high heat distortion temperature, high modulus and high tensile strength as in the present invention.

References

1. D. Dieterich, E. Grigat, W. Hahn, H. Hespe and H. G. Schmelzer, *Polyurethane Handbook*, G. Oertel Ed Hanser/Gardner Publications, 2nd ed. Chap 2 (1993)

2. Z. Wirpsa, Polyurethanes Chemistry, Technology and Applications Ellis Horwood pp118 (1993)
3. F Braun, L. Willner, M Hess and R Kosfeld, *J. Organomet. Chem*, Vol 332, pp 63–68 (1987)

What is claimed is:

1. A non-elastomeric polyurethane composition which includes a first chain extender of the general formula (I):

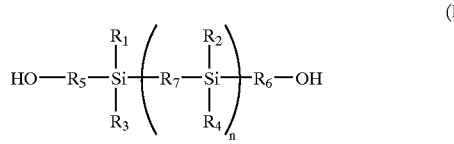

wherein
$R_1$, $R_2$, $R_3$, $R_4$, $R_5$, and $R_6$ are the same or different and selected from an optionally substituted straight chain, branched or cyclic, saturated or unsaturated hydrocarbon radical;
$R_7$ is a divalent linking group or an optionally substituted straight chain, branched or cyclic, saturated or unsaturated hydrocarbon radical; and
n is 0 or greater,
and a second chain extender.

2. The polyurethane composition of claim 1, wherein the chain extender of formula (I) has a molecular weight of about 500 or less.

3. The polyurethane composition of claim 1 wherein the hydrocarbon radical is alkyl, alkenyl, alkynyl, aryl, heterocyclyl, alkylene, alkenylene, or alkynylene.

4. The polyurethane composition of claim 1 wherein the divalent linking group is O, S or NR wherein R is hydrogen or an optionally substituted straight chain, branched or cyclic, saturated or unsaturated hydrocarbon radical.

5. The polyurethane composition of claim 1 wherein the first chain extender of general formula (I) is 1,3-bis(4-hydroxybutyl)-tetramethyl disiloxane wherein $R_1$, $R_2$, $R_3$ and $R_4$ are methyl, $R_5$ and $R_6$ are butyl and $R_7$ is O, 1,4-bis(3-hydroxypropyl)tetramethyl disilylethylene wherein $R_1$, $R_2$, $R_3$ and $R_4$ are methyl, $R_5$ and $R_6$ are propyl and $R_7$ is ethylene, or 1,4-bis(3-hydroxypropyl)tetramethyl disiloxane.

6. The polyurethane composition of claim 1 wherein the second chain extender is 1,4-butanediol, 1,6-hexanediol, 1,8-octanediol, 1,9-nonanediol, 1,10-decanediol, 1,12-dodecanediol, 1,4-cyclohexanedimethanol, 1,4-cyclohexanediol and isomers thereof, hydroxyquinone bis(2-hydroxyethyl)ether, 2-ethyl-1,3-hexanediol, 2-butyl-2-ethyl-1,3-propanediol, 2,2,4-trimethyl-1,3 pentanediol, or mixtures thereof.

7. The polyurethane composition of claim 1 wherein the second chain extender is 1,4-cyclohexanedimethanol or 1,4 butanediol.

8. The polyurethane composition as claimed in claim 1, 2, 3, 4, 5, 6, or 7 which further includes a polyisocyanate.

9. The polyurethane composition of claim 8 wherein the polyisocyanate is a diisocyanate.

10. The polyurethane composition of claim 8 wherein the diisocyanate is an aliphatic or aromatic diisocyanate.

11. The polyurethane composition of claim 9 wherein the diisocyanate is 4,4'-diphenylmethane diisocyanate (MDI), methylene bis(cyclohexyl)diisocyanate ($H_{12}$MDI) or isomers thereof, p-phenylene diidocyanate (p-PDI), trans-cyclohexane-1,4-diisocyanate (CHDI), 1,6-diisocyanatohexane (DICH), 1,6-toluene diisocyanate (2,4-TDI), para-tetramethylxylene diisocyanate (p-TMXDI); meta-tetramethylxylene diisocyanate (m-TMXDI), 2,4- and 2,6-toluene diisocyanate and their isomer mixtures, isophorone diisocyanate, or 1,5-naphthalene diisocyanate.

12. A non-elastomeric polyurethane composition including a reaction product of:
   (i) a polyisocyanate; and
   (ii) the first silicon chain extender and the second chain extender of claim 1.

13. A method of producing a non-elastomeric polyurethane composition including reacting a polyisocyanate with a mixture of chain extenders of claim 1.

14. A material having improved mechanical properties, clarity and/or degradation resistance including a non-elastomeric polyurethane composition which includes the first silicon chain extender and the second chain extender of claim 1.

15. The material of claim 14 which is a biomaterial.

16. A medical device, article or implant composed wholly or partly of the non-elastomeric polyurethane composition defined in claim 1.

17. The medical device, article or implant of claim 1 which is a component of cardiac pacemakers, cardiac assist devices, heart valves, extra-corporeal devices, blood pumps, balloon pumps, A–V shunts, biosensors, artificial joints, or orthopaedic implants.

18. An article composed wholly or partly of the non-elastomeric polyurethane composition as defined in claim 1.

* * * * *